United States Patent
Yoo et al.

(10) Patent No.: US 8,278,472 B2
(45) Date of Patent: Oct. 2, 2012

(54) METHOD OF PREPARING ALLYLCHLOROSILANE DERIVATIVE

(75) Inventors: Bok Ryul Yoo, Seoul (KR); Joon Soo Han, Seongnam Si (KR); Dong Won Lee, Uijeongbu Si (KR)

(73) Assignee: Korea Institute of Science and Technology, Seoul (KR)

( * ) Notice: Subject to any disclaimer, the term of this patent is extended or adjusted under 35 U.S.C. 154(b) by 316 days.

(21) Appl. No.: 12/694,723

(22) Filed: Jan. 27, 2010

(65) Prior Publication Data

US 2011/0130585 A1    Jun. 2, 2011

(30) Foreign Application Priority Data

Nov. 27, 2009  (KR) .................. 10-2009-0116123

(51) Int. Cl.
*C07F 7/08* (2006.01)
(52) U.S. Cl. ....................................... 556/481
(58) Field of Classification Search .................. None
See application file for complete search history.

(56) References Cited

U.S. PATENT DOCUMENTS 6,291,698 B1 * 9/2001 Bade et al. .............. 556/481
6,392,077 B1 * 5/2002 Jung et al. .............. 556/481

OTHER PUBLICATIONS

N. Furuya et al.; "*The condensation reaction of trichlorosilane with allylic chlorides catalyzed by copper salts in the presence of a tertiary amine*"; Journal of Organometallic Chemistry, 96 (1975) pp. C1-C3.
J. Tsuji et al.; "*Organic synthesis by means of noble metal complexes-XCII*"; Tetrahedron, vol. 30, pp. 2143-2146, 1974.
Robert A. Benkeser, et al.; "Chloroplatinic acid catalyzed additions of silanes to isoprene"; Journal of Organometallic Chemistry, 156 (1978) pp. 235-244.
Seung Ho Yeon et al.; "Problems and solutions involved in direct synthesis of allylchlorosilanes"; Organometallics 1993, 12, pp. 4887-4891.
Seung-Hyun Kang et al.; "Phosphonium Chloride—Catalyzed Dehydrochlorinative Coupling Reactions of Alkyl Halides with Hydridochlorosilanes"; "Organometallics" vol. 22; No. 3; pp. 529 ~ 534; American Chemical Society; 2003.
Korean office action dated Jul. 5, 2011 for Korean application No. 10-2009-0116123.

* cited by examiner

*Primary Examiner* — Sudhakar Katakam
(74) *Attorney, Agent, or Firm* — Lowe Hauptman Ham & Berner, LLP

(57) ABSTRACT

Provided is a method of preparing allylchlorosilane, and more particularly, a method of preparing allylchlorosilane with high yield by Si—C coupling reaction of an allyl chloride derivativce with a hydrosilane derivative under specific reaction conditions without using a catalyst.

8 Claims, 3 Drawing Sheets

[Fig. 1]
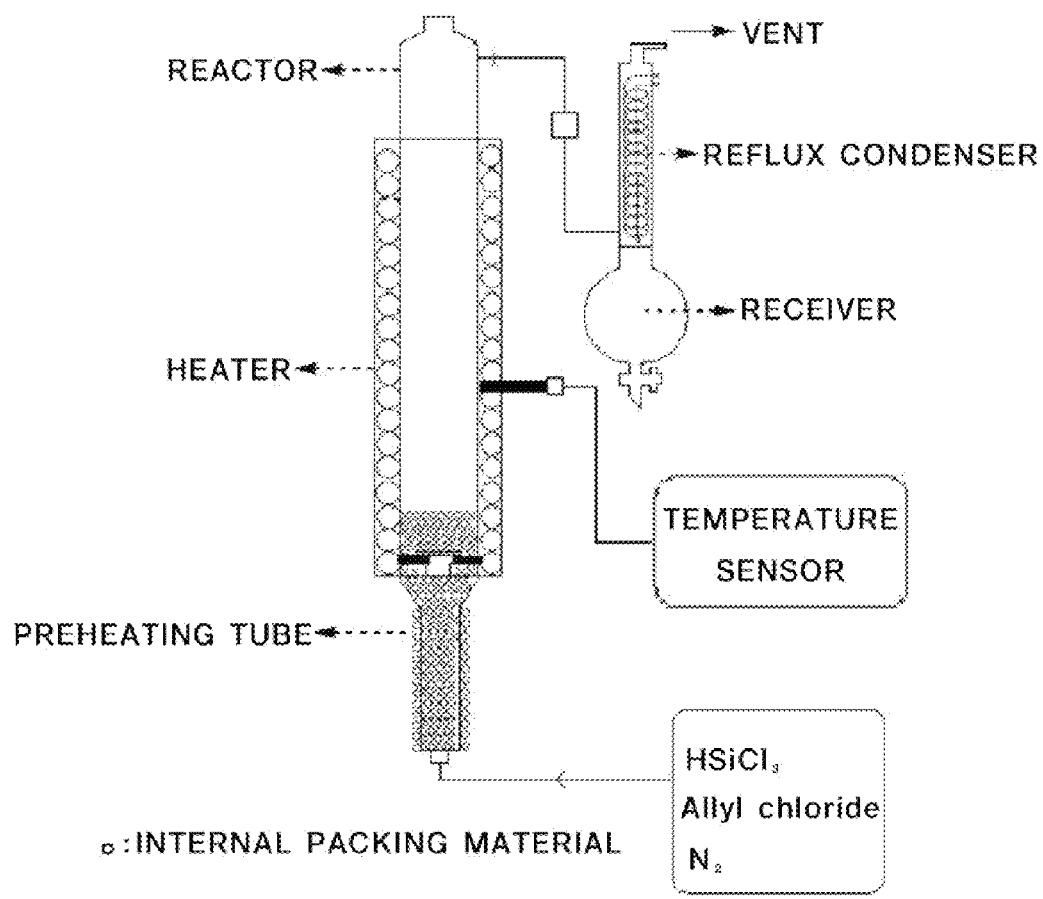

[Fig. 2]
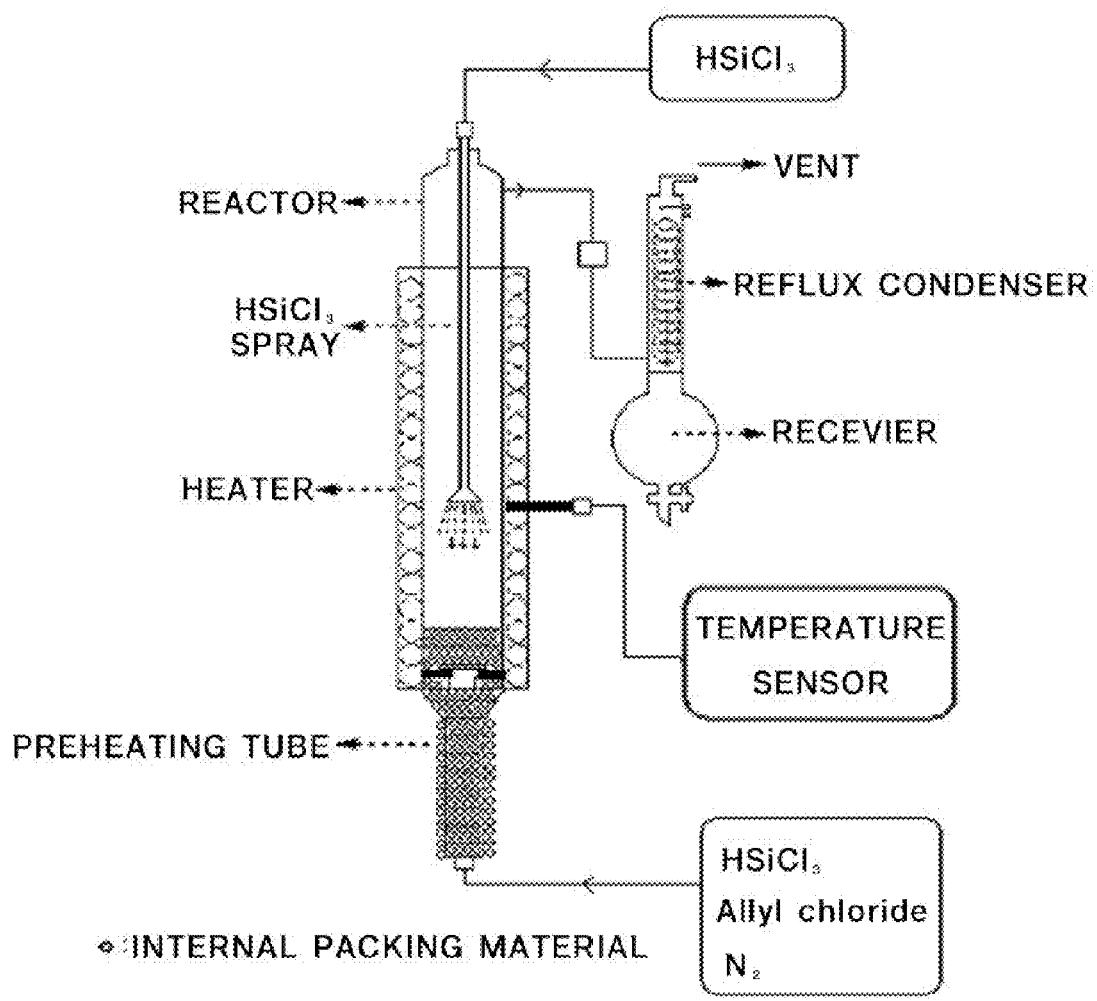

[Fig. 3]
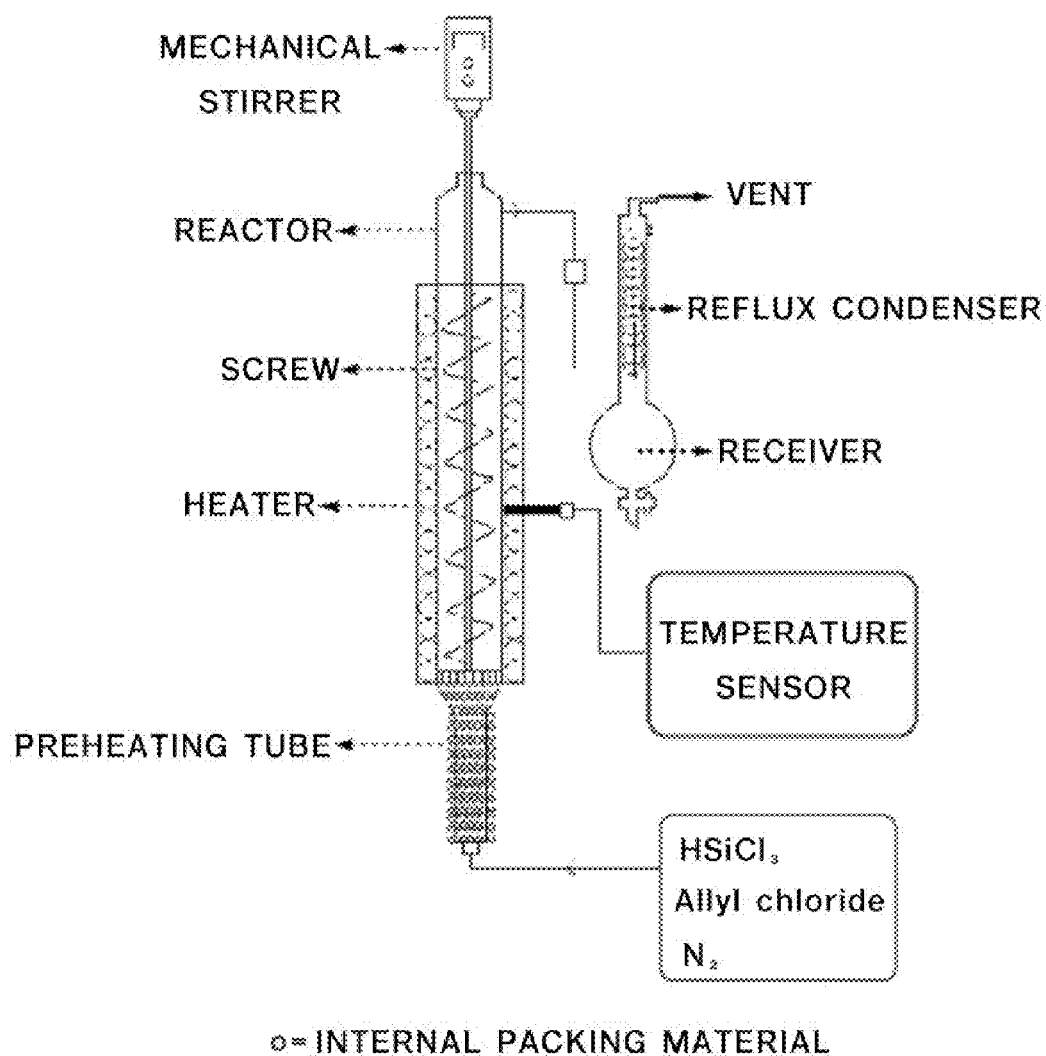

METHOD OF PREPARING ALLYLCHLOROSILANE DERIVATIVE

CROSS-REFERENCE TO RELATED APPLICATION

This application claims under 35 U.S.C. §119(a) the benefit of Korean Patent Application No. 10-2009-0116123 filed Nov. 27, 2009, the entire contents of which are incorporated herein by reference.

BACKGROUND OF THE INVENTION

1. Field of the Invention

The present invention relates to a method of preparing allylchlorosilanes with high yield by Si—C coupling reaction by reacting an allyl chloride derivative with a hydrosilane derivative under specific reaction condition.

2. Description of the Related Art

Allylchlorosilane known as a compound efficiently increasing $C_3$ in organic syntheses can be used as a source of an organic silicon polymer.

As a method of preparing allylchlorosilane derivatives, a method of optionally preparing allyltrichlorosilane derivatives by hydrosilylation of allyl chloride and trichlorosilane in the presence of $CuCl/Et_3N$ catalyst is disclosed (N. Furuya, T. Sukawa *J. Organomet. Chem.* 1975, 96, C1-C3). This synthesis method is efficient in laboratory scale reaction, but not suitable for mass production. In the reaction using $CuCl/NR_3$ catalyst, a large amount of tertiary amine should be used as a scavanger to remove HCl that is produced as a by-product. In this case, a large amount of amine salts, as by-products, are produced, making the process for isolating allyltrichlorosilane complicated, thereby increasing the cost for recycling the amine salts.

2-Butenylchlorosilane may be prepared by hydrosilylation of a butadiene derivative (butadiene or isoprene) with a hydrosilane in the presence of a Group 10 metal catalyst. For example, (Z)-crotyltrichlorosilane may be synthesized with a yield of 84% by the reaction of trichlorosilane with butadiene in the presence of a palladium catalyst $[Pd(PPh_3)_4]$ at 100° C. for 5 hours. Under the same conditions, a mixture of 2-methyl-2-butenyltrichlorosilane (82%) and 3-methyl-2-butenyltrichlorosilane (3%) may be synthesized by the reaction of trichlorosilane with isoprene at 100° C. for 6 hours (J. Tsuji, M. Hara, K. Ohno, Tetrahedron, 1974, 30, 2143). A method of preparing a mixture of 2-methyl-2-butenylchlorosilane and 3-methyl-2-butenylchlorosilane by the hydrosilylation of isoprene with a hydrosilane ($HSiX_3$, where $X_3$ is $Cl_3$, $MeCl_2$, or $Me_2Cl$) in the presence of a platinic acid catalyst ($H_2PtCl_6$) at 165° C. has been reported (R. A. Benkesser, et. al. *J. Organomet. Chem.* 1978, 156, 235-244). However, since a reactant with low boiling point (butadiene b.p.: -4.4° C.; $HSiCl_3$: 31° C.) is used in the synthesis of allylchlorosilane by hydrosilylation, a high-pressure reactor or a sealed tube is required. In addition, since an expensive palladium or platinum catalyst is used, the manufacturing costs are high.

Another method of synthesizing allylchlorosilanes with a yield of 31% by directly reacting a mixed gas of allyl chloride and HCl with metallic silicon in the presence of a copper (Cu) catalyst (with a cadmium (Cd) cocatalyst) at 260° C. has been reported (S. H. Yeon, B. W. Lee, S.-I. Kim, I. N. Jung, Organometallics, 1993, 12, 4887). This method may be continuously performed, but the yield is low.

Since these conventional methods of preparing allylchlorosilanes as described above are not suitable for mass production, the need for a method of preparing allylchlorosilane suitable for mass production is increasing.

SUMMARY OF THE INVENTION

While searching for an economical preparing method of allylchlorosilanes, the present inventors found that synthetic conditions for directly preparing allylchlorosilane derivatives without using a catalyst. The present invention relates to a method of preparing allylchlorosilanes in a cost-effective manner without using a catalyst.

According to an aspect of the present invention, there is provided a method of preparing allylchlorosilane represented by Formula 1 by reacting an allyl chloride derivative represented by Formula 2 with a hydrosilane derivative represented by Formula 3 under high-temperature gaseous condition by Si—C coupling reaction:

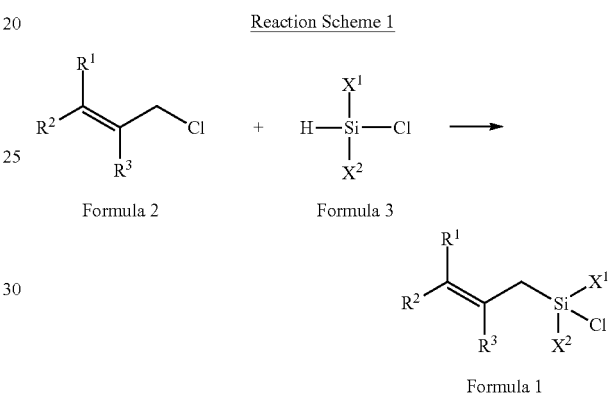

Reaction Scheme 1 wherein $R^1$, $R^2$ and $R^3$, which are same or different, are each independently a hydrogen atom or a methyl group, and $X^1$ and $X^2$, which are same or different, are each independently a hydrogen atom, a chlorine atom, or a methyl group.

BRIEF DESCRIPTION OF THE DRAWINGS

The above and other features and advantages of the present invention will become more apparent by describing in detail exemplary embodiments thereof with reference to the attached drawings in which:

FIG. 1 illustrates a filling material-type reactor prepared according to Example 1 according to an embodiment of the present invention;

FIG. 2 illustrates a spray-filling material-type reactor prepared according to Example 4 according to an embodiment of the present invention; and FIG. 3 illustrates a reactor including a screw-type stirrer prepared according to an embodiment of the present invention.

DETAILED DESCRIPTION OF THE INVENTION

Hereinafter, the present invention will be described in more detail with reference to exemplary embodiments of the invention.

According to an embodiment of the present invention, a method of preparing allylchlorosilanes represented by Formula 1 via Si—C coupling reaction by reacting an allyl chloride derivative represented by Formula 2 with a hydrosilane derivative represented by Formula 3 under high-temperature gaseous condition is provided.

Reaction Scheme 1

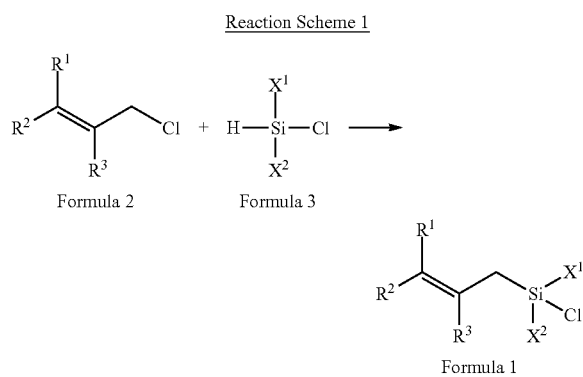

In Reaction Scheme 1, $R^1$, $R^2$ and $R^3$, which are same or different, are each independently a hydrogen atom or a methyl group, and $X^1$ and $X^2$, which are same or different, are each independently a hydrogen atom, a chlorine atom, or a methyl group.

The method according to the present embodiment includes: a first step of mixing the allyl chloride derivative and the hydrosilane derivative in a liquid or gaseous phase; and a second step of adding the mixture into a reactor and performing the Si—C coupling reaction at a temperature from 400 to 650° C. at a pressure of 1 to 3 bar.

In the first step, the allyl chloride derivative and the hydrosilane derivative are pre-mixed in a liquid or gaseous phase to form a uniform mixture without using a separate device. The molar ratio of the allyl chloride derivative to the hydrosilane derivative may be in the range of 1:1 to 8, preferably 1:1 to 5, and more preferably 1:1 to 3. In this regard, if the molar ratio of the allyl chloride derivative to the hydrosilane derivative is less than 1:1, the yield of the allylchlorosilane may be reduced. On the other hand, if the molar ratio of the allyl chloride derivative to the hydrosilane derivative is greater than 1:8, the increase of the yield of the allylchlorosilane is negligible.

In addition to the compound represented by Formula 2, the allyl chloride derivative may also be at least one selected from the group consisting of 1-chloro-2-propene, 1-chloro-2-butene, 1-chloro-2-methyl-2-propene, 1-chloro-3-methyl-2-butene, and 1-chloro-2,3-dimethyl-2-butene, but is not limited thereto. In addition to the compound represented by Formula 3, the hydrosilane derivative may also be at least one selected from the group consisting of trichlorosilane, methyldichlorosilane, and dimethylchlorosilane, but is not limited thereto.

In addition, the allyl chloride derivative and the hydrosilane derivative are passed through a preheating tube completely filled with a packing material selected from the group consisting of a glass bead and a metal chip at a temperature from 150 to 350° C., and preferably 150 to 250° C. in the first step to introduce the allyl chloride derivative and the hydrosilane derivative into the reactor in which the second step is performed. Here, if the temperature of the preheating tube is below 150° C., it is difficult to maintain a desired temperature of the reactor since reactants having a low temperature are introduced into the reactor. On the other hand, if the temperature of the preheating tube is greater than 350° C., the reactants may react not in the reactor but in the preheating tube. Then, the mixture that is obtained in the preheating tube and has a gaseous phase is added to the reactor in which the second step is performed.

The second step, in which the Si—C coupling reaction of the mixture obtained in the first step is performed to prepare the allylchlorosilane of Formula 1, may be performed at a temperature from 400 to 650° C. and at a pressure ranging from 1 to 3 bar, and preferably at a temperature from 450 to 550° C. and at a pressure ranging from 1 to 2 bar. Since the reaction between the hydrosilane derivative and the allyl chloride derivative is a high temperature reaction, the reactor needs to be efficiently heated to control the reaction temperature. In the reactor, the temperature of an inlet of the reactor through which reactants are supplied may be low, and the temperature of an outlet through which the reactants are discharged may be high since the reactants are heated while passing through the reactor. In order to prevent this temperature difference, the temperature of the inlet of the reactor needs to be controlled. In addition, if the temperature of the reactor is less than 400° C., the Si—C coupling reaction may not be sufficiently performed, thereby reducing the yield of the product. On the other hand, if the temperature of the reactor is greater than 650° C., the reactants or products are polymerized and deposited on the filling material in a black solid phase, or a double bond of the allylchlorosilane, as a product, migrates to be converted into a vinylsilane. Furthermore, if the pressure of the reactor is less than 1 bar, a time period during which the reactants stay in the reactor is reduced, so that the reaction time may not be sufficient. On the other hand, if the pressure of the reactor is greater than 3 bar, the reactants and products may be polymerized in the reactor. In addition, if the mixture that passed through the preheating tube is supplied to the reactor in a vaporized (gaseous) phase, and the supplying rate may be in the range of 2 to 15 cm/sec.

A nitrogen ($N_2$) gas may also be supplied to the reactor to increase the yield in the second step. In this regard, the nitrogen ($N_2$) gas may be simultaneously supplied to the reactor with the mixture through the preheating tube, or with an additional pipe. The nitrogen ($N_2$) gas may be supplied to the reactor at a rate ranging from 0.1 to 2 mL/min, preferably 0.1 to 1.5 mL/min, and more preferably 0.2 to 1 mL/min. If the rate of supplying the nitrogen ($N_2$) gas is less than 0.1 mL/min, the yield of the allylchlorosilane is not increased. On the other hand, if the rate of supplying the nitrogen ($N_2$) gas is greater than 2 mL/min, the effects of the increase in the nitrogen ($N_2$) gas is negligible.

In the second step, the reactants and products may stay in the reactor for 2 to 6 seconds. If the reactants and products stay in the reactor for longer than 6 seconds, side reactions such as polymerization may be performed.

The reactor for the method according to the present embodiment may be any reactor that is commonly used in the art, for example, a packed-column type reactor illustrated in FIG. 1, a spray-packed-column-type reactor illustrates in FIG. 2, or a reactor including a screw-type stirrer illustrated in FIG. 3, but is not limited thereto.

The filling material-type reactor will be described in more detail. The packed-column type reactor as illustrated in FIG. 1 may include a preheating tube, a heater, a reactor, a reflux condenser, and a receiver. A spray may be installed in the packed-column type reactor to prepare the spray-packed-column-type reactor as illustrated in FIG. 2. The preheating tube that is a device vaporizing the mixture of the allyl chloride derivative and the hydrosilane derivative, as reactants, before the mixture is supplied into the reactor, is filled with a filling material selected from the group consisting of a glass bead and a metal chip. Through the preheating tube, the nitrogen ($N_2$) gas may be supplied with the mixture. The heater is a device to maintain a temperature suitable for the Si—C coupling reaction. The spray is a device to inhibit or prevent the polymerization of the allylchlorosilane derivatives by spraying the hydrosilane derivative represented by Formula 3. The amount of the hydrosilane derivative may be in the range of 0.1 to 2 times of the weight of the allyl chloride derivative that is supplied to the preheating tube. After the Si—C coupling reaction is performed in a reaction bath, products are obtained using the reflux condenser. The reaction bath of the reactor may be used without the filling material. Alternatively, the reaction bath may be filled with the filling material selected from the group consisting of a glass bead and a chip to 1 to 90% of the height of the reaction bath to have a large contact area at high temperature, thereby efficiently performing the reaction. The reaction bath may be made of quartz glass or stainless steel.

The reactor including a screw-type stirrer that is designed to increase the yield of products by optimizing the Si—C coupling reaction, may include a preheating tube, a heater, a reflex condenser, a receiver, and a screw-type stirrer. The screw-type stirrer may mix the reactants at a rate ranging from 30 to 300 rpm/min, and preferably, 50 to 200 rpm/min to efficiently mix the reactants.

The present invention will be described in further detail with reference to the following examples. These examples are for illustrative purposes only and are not intended to limit the scope of the present invention.

EXAMPLES

Example 1

(1) Preparation of Packed-Column-Type Reactor

A packed-column-type reactor including a preheating tube filled with a packing material (316SS manufactured by CAN-NON, 150 to 350° C.), a reactor filled with a packing material (316SS manufactured by CANNON, 400 to 650° C.), a reflux condenser (−20° C.), and a receiver was prepared.

A quartz glass tube having an inner diameter of 37 mm and a height of 60 cm was used as the reactor, a temperature sensor using type K chromel-alumel thermocouple was disposed at the center of the reactor to measure the temperature of the reactor, and a heater was installed out of the reactor to control the reaction temperature. A pyrex glass tube having an inner diameter of 37 mm and a length of 30 mm was used as the preheating tube. The preheating tube was surrounded with heating wires to control the temperature of the preheating tube using an automatic temperature control system, and disposed at a lower end of the reactor. Then, the reactants and products stayed in the reactor for about 4 to 5 seconds.

(2) Preparation of Allylchlorosilane

Trichlorosilane (1a) was mixed with allyl chloride (2a) using the reactor illustrated in FIG. 1. Then, the mixture was supplied to the reactor via the preheating tube at a rate of 2.7 g/min, and a nitrogen ($N_2$) gas was supplied to the reactor via the preheating tube at a rate of 0.5 mL/min at 230° C. Allylchlorosilane was prepared while varying the molar ratio of trichlorosilane (1a) to allyl chloride (2a) and conditions for the reaction as shown in Table 1 below. The conversion rate of allyl chloride and the yield of products were obtained using gas chromatography, and the results are shown in Table 1.

TABLE 1

| Example | Height of filling material of reactor (cm) | Molar ratio of 2a:1a | Reaction temp. (° C.) | Conversion rate of 2a (%) | Yield of product (%)[1] allylchlorosilane $CH_2$=$CHCH_2SiCl_3$ | vinylchlorosilane $CH_2CH$=$CHSiCl_3$ |
|---|---|---|---|---|---|---|
| 1-1 | 0 | 1:3 | 500 | 81 | 66 | 7 |
| 1-2 | 0 | 1:3 | 550 | 86 | 40 | 11 |
| 1-3 | 2 | 1:3 | 500 | 86 | 58 | 7 |
| 1-4 | 5 | 1:3 | 450 | 71 | 88 | 5 |
| 1-5 | 5 | 1:3 | 470 | 82 | 81 | 8 |
| 1-6 | 5 | 1:3 | 500 | 85 | 79 | 8 |
| 1-7 | 5 | 1:3 | 550 | 87 | 74 | 9 |
| 1-8 | 10 | 1:1.5 | 430 | 25 | 95 | 0 |
| 1-9 | 10 | 1:1.5 | 470 | 66 | 75 | 10 |
| 1-10 | 10 | 1:1.5 | 500 | 71 | 77 | 5 |
| 1-11 | 30 | 1:1.5 | 430 | 53 | 85 | 4 |
| 1-12 | 30 | 1:1.5 | 440 | 60 | 64 | 2 |
| 1-13 | 30 | 1:1.5 | 450 | 64 | 67 | 5 |

[1]obtained based on the amount of allyl chloride (2a) consumed.

Example 2

Allylchlorosilane was prepared in the same manner as in Example 1, except that methyldichlorosilane (1b) was used instead of trichlorosilane (1a). The mixture was supplied to the reactor via the preheating tube at a rate of 4.5 g/min, and a nitrogen ($N_2$) gas was supplied to the reactor via the preheating tube at a rate of 0.5 mL/min. The conditions for the reaction and the results are listed in Table 2 below.

TABLE 2

| Example | Height of filling material of reactor (cm) | Molar ratio of 2a:1b | Reaction temp. (° C.) | Conversion rate of 2a (%) | Yield of product (%)[1] allylchlorosilane $CH_2$=$CHCH_2SiCH_3Cl_2$ | vinylchlorosilane $CH_2CH$=$CHSiCH_3Cl_2$ |
|---|---|---|---|---|---|---|
| 2-1 | 5 | 1.5 | 500 | 89 | 45 | 2 |
| 2-2 | 10 | 1.5 | 520 | 73 | 55 | 10 |

[1]obtained based on the amount of allyl chloride (2a) consumed.

Example 3

Allylchlorosilane was prepared in the same manner as in Example 1, except that dimethylchlorosilane (1c) was used instead of trichlorosilane (1a). The mixture was supplied to the reactor via the preheating tube at a rate of 4.5 g/min, and a nitrogen ($N_2$) gas was supplied to the reactor via the preheating tube at a rate of 0.5 mL/min. The conditions for the reaction and the results are listed in Table 3 below.

TABLE 3

| Example | Height of filling material of reactor (cm) | Molar ratio of 2a:1c | Reaction temp. (° C.) | Conversion rate of 2a (%) | Yield of product (%)[1] allylchlorosilane $CH_2$=$CHCH_2Si(CH_3)_2Cl$ | vinylchlorosilane $CH_2CH$=$CHSi(CH_3)_2Cl$ |
|---|---|---|---|---|---|---|
| 3-1 | 5 | 1.5 | 500 | 58 | 79 | 20 |
| 3-2 | 10 | 1.5 | 520 | 82 | 45 | 12 |

[1]obtained based on the amount of allyl chloride (2a) consumed.

Example 4

A spray-packed-column-type reactor having a height of 30 cm illustrated in FIG. 2 was prepared in the same manner as in Example 1, except that a spraying-tube for spraying an allyl chloride derivative (1a) is installed at a height of 15 cm from the lower end of the reactor. Using this spray-packed-column-type reactor, allylchlorosilane was prepared in the same manner as in Example 1 under the conditions listed in Table 4 below. The mixture of trichlorosilane (1a) and allyl chloride (2a) was supplied to the preheating tube at a rate of 4.5 g/min, and trichlorosilane (1a') was supplied to the reactor using the spray at a rate of 1.2 g/min such that the amount of the trichlorosilane (1a') is 0.33 times of that of trichlorosilane (1a) contained in the mixture.

TABLE 4

| Example | Height of filling material of reactor (cm) | Molar ratio of 2a:1a | Reaction temp. (° C.) | Conversion rate of 2a (%) | Yield of product (%)[1] allylchlorosilane $CH_2$=$CHCH_2SiCl_3$ | vinylchlorosilane $CH_2CH$=$CHSiCl_3$ |
|---|---|---|---|---|---|---|
| 4-1 | 3 | 1:3 | 500 | 32 | 87 | 0 |
| 4-2 | 3 | 1:3 | 550 | 73 | 75 | 13 |
| 4-3 | 10 | 1:3 | 450 | 38 | 57 | 0 |
| 4-4 | 10 | 1:3 | 500 | 74 | 82 | 16 |
| 4-4[2] | 10 | 1:3 | 500 | 78 | 74 | 14 |
| 4-5 | 20 | 1:3 | 430 | 77 | 56 | 0 |

[1]obtained based on the amount of allyl chloride (2a) consumed.
[2]a reactor having a height of 60 cm is used, wherein experiments were performed in the same manner as in Examples 4-1 to 4-5, except that trichlorosilane (1a) was sprayed at a height of 30 cm)

Example 5

Allylchlorosilane was prepared in the same manner as in Example 4, except that methyldichlorosilant (1b) was used instead of trichlorosilane (1a) under the conditions listed in Table 5 below.

TABLE 5

| Example | Height of filling material of reactor (cm) | Molar ratio of 2a:1b | Reaction temp. (° C.) | Conversion rate of 2a (%) | Yield of product (%)[1] allylchlorosilane $CH_2=CHCH_2Si(CH_3)_2Cl$ | vinylchlorosilane $CH_2CH=CHSi(CH_3)_2Cl$ |
|---|---|---|---|---|---|---|
| 5 | 10 | 1:3 | 520 | 72 | 57 | 4 |

[1]obtained based on the amount of allyl chloride (2a) consumed.

Example 6

Allylchlorosilane was prepared in the same manner as in Example 4, except that dimethylchlorosilane (1c) was used instead of trichlorosilane (1a) under the conditions listed in Table 6 below.

TABLE 6

| Example | Height of filling material of reactor (cm) | Molar ratio of 2a:1c | Reaction temp. (° C.) | Conversion rate of 2a (%) | Yield of product (%)[1] allylchlorosilane $CH_2=CHCH_2SiCH_3Cl_2$ | vinylchlorosilane $CH_2CH=CHSiCH_3Cl_2$ |
|---|---|---|---|---|---|---|
| 6 | 10 | 1:3 | 520 | 81 | 58 | 4 |

[1]obtained based on the amount of allyl chloride (2a) consumed.

Example 7

(1) Preparation of Reactor Including a Screw-Type Stirrer

A spray type reactor including a preheating tube filled with a packing material (316SS manufactured by CANNON, 150 to 350° C.), a reactor (400 to 650° C.), a reflux condenser (−20° C.), a receiver, and a screw-type stirrer was prepared as shown in FIG. 3.

A quartz glass tube having an inner diameter of 37 mm and a height of 30 cm was used as the reactor, a temperature sensor using type K chromel-alumel thermocouple was disposed at the center of the reactor to measure the temperature of the reactor, and a heater was installed out of the reactor to control the reaction temperature. A pyrex glass tube having an inner diameter of 37 mm and a length of 30 mm was used as the preheating tube. The preheating tube was surrounded with heating wires to control the temperature of the preheating tube using an automatic temperature control system, and disposed at a lower end of the reactor. Then, the reactants and products stayed in the reactor for about 4 to 5 seconds.

In addition, the stirrer that was formed of stainless steel was prepared by applying screw shaped blades having a radius of 12 mm to a bar having a height of 20 cm and a diameter of 5 mm. Then, the stirrer was installed in the reactor such that the stirrer was spaced apart from the reactor by 3 mm, and operated at a rate of 100 rpm/min.

(2) Preparation o Allylchlorosilane

Trichlorosilane (1a) was mixed with allyl chloride (2a) using the reactor including the screw-type stirrer, the mixture was supplied to the reactor via the preheating tube at a rate of 4.5 g/min, and a nitrogen ($N_2$) gas was supplied to the reactor via the preheating tube at a rate of 0.5 mL/min at 200° C. Allylchlorosilane was prepared while varying the molar ratio of trichlorosilane (1a) to allyl chloride (2a) and conditions for the reaction as shown in Table 7 below.

TABLE 7

| Example | Molar ratio of 2a:1a | Stirring rate (rpm/min) | Reaction temp. (° C.) | Conversion rate of 2a (%) | Yield of product (%)[1] $CH_2=CHCH_2SiCl_3$ | $CH_2CH=CHSiCl_3$ |
|---|---|---|---|---|---|---|
| 7-1 | 1:3 | 0 | 500 | 88 | 70 | 8 |
| 7-2 | 1:3 | 10 | 500 | 86 | 71 | 9 |
| 7-3 | 1:3 | 50 | 500 | 81 | 82 | 6 |
| 7-4 | 1:3 | 100 | 500 | 79 | 88 | 5 |

[1]obtained based on the amount of allyl chloride (2a) consumed.

Referring to Tables 1 to 7, it is identified that allylchlorosilane may be produced with high yield. Even though the Si—C coupling reaction is performed without a catalyst, allylchlorosilane may be produced with high yield using the method according to the present invention. Therefore, allylchlorosilane can be econmically prepared using the method according to the present invention.

As described above, according to the present invention, allylchlorosilane can be economically prepared with high yield since an expensive catalyst is not required. Thus, the method of preparing allylchlorosilane according to the present invention is suitable for a large scale production.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of preparing allylchlorosilane represented by Formula 1, the method comprising:
   mixing the allylchlorideallyl chloride derivative and the hydrosilane derivative in a liquid or gaseous phase;
   adding the mixture into a reactor; and
   reacting an allylchloride derivative represented by Formula 2 with a hydrosilane derivative represented by Formula 3 at a temperature from 400 to 650° C. and at a pressure of 1 to 3 bar gaseous condition by Si—C coupling reaction:

$(R^1R^2)C\!=\!C(R^3)\!-\!CH_2\!-\!Si\,(X^1X^2)\!-\!Cl$ (1), $H\!-\!Si\,(X^1X^2)\!-\!Cl$ (2), $(R^1R^2)C\!=\!C(R^3)\!-\!CH_2\!-\!Cl$ (3), wherein $R^1$, $R^2$ and $R^3$, which are same or different, are each independently a hydrogen atom or a methyl group, and $X^1$ and $X^2$, which are same or different, are each independently a hydrogen atom, a chlorine atom, or a methyl group, and the reactants and products stay in the reactor for 2 to 6 seconds.

2. The method of claim 1, wherein the first step is performed in a preheating tube filled with a filling material selected from the group consisting of a glass bead and a metal filler at a temperature from 150 to 350° C.

3. The method of claim 1, wherein the molar ratio of the allylchloride derivative to the hydrosilane derivative in the first step is in the range of 1:1 to 8.

4. The method of claim 1, wherein the mixture and a nitrogen ($N_2$) gas are simultaneously supplied to the reactor in the second step, wherein the nitrogen ($N_2$) gas is supplied into the reactor at a rate ranging from 0.1 to 2 mL/min.

5. The method of claim 1, wherein the reactor is filled with a packing material selected from the group consisting of a glass bead and a metal chip to 1 to 90% of the height of the reactor in the second step.

6. The method of claim 1, wherein the reactor comprises a spraying-tube.

7. The method of claim 6, wherein the hydrosilane derivative represented by Formula 3 is further added to the reactor using a spraying-tube in order to prevent the allylchlorosilane derivative represented by Formula 1, as a product, from being polymerized, wherein the amount of the hydrosilane that is further added is in the range of 0.1 to 2 times of the weight of the hydrosilane derivative contained in the mixture:

$(R^1R^2)C\!=\!C(R^3)\!-\!CH_2\!-\!Si(X^1X^2)\!-\!Cl$ (1), $H\!-\!Si(X^1X^2)\!-\!Cl$ (2), $(R^1R^2)C\!=\!C(R^3)\!-\!CH_2\!-\!Cl$ (3), wherein $R^1$, $R^2$ and $R^3$, which are same or different, are each independently a hydrogen atom or a methyl group, and $X^1$ and $X^2$, which are same or different, are each independently a hydrogen atom, a chlorine atom, or a methyl group.

8. The method of claim 1, wherein the reactor comprises a screw-type stirrer in the second step.

* * * * *